United States Patent [19]

Kalasek

[11] 4,192,845

[45] Mar. 11, 1980

[54] STERILIZATION PROCESS AND APPARATUS FOR INFUSION SOLUTIONS AND THE LIKE FILLED IN CONTAINERS

[75] Inventor: Karl Kalasek, Vienna, Austria

[73] Assignee: Firma Vereinigte Edelstahlwerke Aktiengesellschaft, Vienna, Austria

[21] Appl. No.: 890,202

[22] Filed: Mar. 27, 1978

[30] Foreign Application Priority Data

Apr. 1, 1977 [AT] Austria .................................. 2301/77

[51] Int. Cl.² ........................... A61L 1/00; A61L 3/00
[52] U.S. Cl. ........................................ 422/25; 422/26; 422/108; 422/109; 422/110; 422/116; 422/297; 422/302
[58] Field of Search ................... 422/25, 26, 108, 109, 422/110, 111, 116, 297, 302

[56] References Cited

U.S. PATENT DOCUMENTS

| | | | |
|---|---|---|---|
| 2,868,616 | 1/1959 | Poitras | 422/25 |
| 2,870,024 | 1/1959 | Martin | 422/302 X |
| 3,088,180 | 5/1963 | Lauterbach | 422/25 |
| 3,366,442 | 1/1968 | Neiss | 422/25 X |
| 3,531,300 | 9/1970 | Greenberg et al. | 422/25 X |
| 3,619,126 | 11/1971 | Carvallo | 422/25 |
| 3,861,872 | 1/1975 | MacFarlane | 422/25 |
| 3,897,818 | 8/1975 | Champel | 422/25 X |
| 3,917,450 | 11/1975 | Martensson et al. | 422/297 X |
| 4,088,444 | 5/1978 | Byrne | 422/25 |

FOREIGN PATENT DOCUMENTS

132909 9/1951 Sweden .................................. 422/304

*Primary Examiner*—Barry S. Richman
*Attorney, Agent, or Firm*—Ernest F. Marmorek

[57] ABSTRACT

A sterilization apparatus includes a housing adapted for receiving a removable rack with open shelves supporting containers with the substance to be sterilized, a fan arranged at the top of the housing, and a cooling device for subsequent cooling of the sterilizing fluid introduced into the housing. To increase the uniformity of whirling of the fluid around the containers on different levels of the rack and thus to increase the heat transfer to, and the subsequent heat removal from the containers, a timing-and flow-controlling device is provided for cyclically changing the flow of the sterilizing fluid through the rack during the heating-up and cooling-down of the sterilization cycle, either by alternating the direction of the flow, or by distributing periodically partial streams through different shelves of the rack.

11 Claims, 7 Drawing Figures

STERILIZATION PROCESS AND APPARATUS FOR INFUSION SOLUTIONS AND THE LIKE FILLED IN CONTAINERS

BACKGROUND OF THE INVENTION

The invention relates generally to sterilization devices, and more particularly it relates to a sterilization apparatus for infusion solutions and the like, stored in containers arranged on open shelves of a displaceable rack; the apparatus is of the type that employs a closed housing adapted for receiving the rack with the containers and within the housing, a fan for whirling around a heated gaseous working medium or fluid, and a cooling device for subsequent indirect cooling of the whirling operating fluid. Sterilization devices of this kind are described for example, in the journal "Die Pharmazeutische Industrie" 1975 Volume 10/pages 825–829, Volume 11/pages 909–912, Volume 12/pages 1071–1075.

In this apparatus, saturated steam, if necessary mixed with air, is introduced as the operating medium or fluid, or whirled air is heated directly in the apparatus. In employing steam it is necessary to avoid a sudden pressure drop during cooling, due to the condensation of steam that might entail a risk of explosion of the hot container exposed to a high inside pressure, by admixing air or other gaseous media.

An increased need for sterile infusion solutions and the like requires as economic an operation of sterilization devices as possible under strict requirements, and furthermore, in order to prevent damage of mostly extremely sensitive substances to be sterilized, the prescribed operational conditions during the entire operating time must be exactly fulfilled. The strictness of maintaining the prescribed operating conditions in sterilizing has been still further increased in view of the development of new and still more sensitive sterilization solutions and the like, and also to diminish erroneous handling in sterilizing conventional substances. It is especially important that the time period during which the sterilized substance is subjected to high temperatures be reduced to such a short sterilizing time as is absolutely necessary in order to avoid any damage; that means that the heating and the cooling of the apparatus must be as rapid as possible, or in other words, a reduction of the heating and cooling periods is necessary.

It has been found that by making use of a hitherto conventional and substantially uniform whirling movement of the operating fluid around the substance to be sterilized, certain values of the heating-up and cooling-down times may not be exceeded. Since the hot operating medium streaming through the rack supporting the containers of the sterilization devices, for example from below the rack to above the rack, transfers more heat at its point of entry than at its point of exit, the containers located on the lower-most shelf of the rack are heated to the sterilization temperatures more quickly, than the containers located on the uppermost shelf. The sterilization time to be maintained can naturally be counted from that point only at which all containers have reached the sterilization temperature. As in the subsequent cooling step the cooled operating medium absorbs more heat from the hot containers in the vicinity of its inlet point than near its outlet point, nonetheless, the heating and the cooling times of the containers follow different characteristic curves, and consequently containers arranged on different shelves of the rack are unavoidably subjected to the sterilizing temperature for different time periods.

SUMMARY OF THE INVENTION

The primary object of this invention is therefore to avoid the above mentioned disadvantages of conventional sterilizing devices of this type, it being specifically an object of this invention to reduce the differences of sterilizing times that occur in the containers arranged on different shelves of the rack.

Another object of this invention is to insure maximum uniformity of handling of the entire product to be sterilized.

Still another object of this invention is to permit an operator to meet exactly the prescribed effective treatment intervals.

According to the present invention, these and other objects explained hereinbelow, are attained by providing a timing-and controlling-device by means of which the flow of the operating medium whirling around the containers with the substance to be sterilized inside the apparatus is cyclically changed, at least during the heating-up and the cooling-down of the containers; the change may take place either sequentially in a predetermined order by changing alternately the direction of flow of the operating medium between the shelves of the rack, or simultaneously by directing partial streams of the medium in different directions through the rack. In comparison to the prior art of uniform movement of the whirling operating medium, the invention results in an increased uniformity of the heat transfer to, or of the heat removal from, all locations of the rack.

In a simple embodiment of this invention a timing and controlling device cyclically changes the direction of flow of the operating fluid through the rack at time intervals which are short relative to the whole heating-up or cooling-down time. For example, the direction of the flow of the operating medium is alternately reversed, so that the heated or cooled operating medium enters alternately from opposite sides of the container supporting rack.

In a preferred embodiment of this invention the stream of the operating fluid branches out, and in different branches there are arranged adjustable valves, lids, sliders, or similar controlling members, which due to the influence of the timing and controlling device alternately open and close the entrance into respective shelves of the rack. In this way different branches of the stream of the operating fluid are opened in consecutive order, and alternately flow through in different directions through different shelves of the rack. Optimum positions of controlling members assigned to different branches of the stream path can be ascertained by simple tests and measurements of a given configuration and size of the rack, and the apparatus housing. In the same manner optimum switching times and switching sequences within each sterilization cycle can be ascertained.

According to another exemplary embodiment of this invention, the various controlling members such as valves, sliders and the like, of the apparatus, utilizing a branched out flow path of the operating medium can be controlled by regulating units, connected in turn to a computer or data processing device, which processes measured data from temperature sensors arranged at different points in the rack. In this manner the partial streams of the operating medium, that in this case may flow through the shelves of the rack continuously, and at the same time from different directions, are automatically controlled by the controlling device as to their intensity, so that the temperature differences at the detected points in the rack are minimized.

It is possible, within the scope of this invention, as a result of the aforedescribed unification of the temperature increase during the heating-up period and the temperature drop during the cooling-down period, to still further substantially cut down the transition times by reducing both the heating-up, as well as the cooling-down periods of the apparatus.

For this purpose the apparatus housing is, in a preferred embodiment of the invention, surrounded by a jacket defining an interspace between the jacket and the housing. The interspace, prior to the loading of the apparatus with the containers, is heated by means of an auxiliary heating medium approximately to the sterilization temperature, and upon expiration of the sterilization time, is cooled down by a cooling medium approximately to the discharge temperature of the containers. In this manner it is no longer necessary to heat-up or to cool-down the entire apparatus with its contents by means of the whirling operating medium, so that the entire time of keeping the containers within the apparatus more nearly approaches the sterilization time proper.

In a process of sterilizing articles stacked on different levels in a closed chamber for a sterilization cycle, and wherein the sterilization cycle includes heating-up and cooling-down periods, the steps advantageously include introducing a stream of a heated sterilization fluid into the chamber, whirling the fluid around the articles, and alternately changing the direction of the stream during time intervals that are short relative to the heating-up and cooling-down periods of the sterilization cycle.

It is preferable for the steps to include dividing the stream of the fluid into at least two partial streams, and periodically directing the partial streams to the different levels of the stacked articles.

It is further advantageous if the steps include sensing the temperature on the different levels, comparing the sensed values to a predetermined average temperature, and directing the partial streams to the levels in response to corresponding differences between the sensed values and the predetermined average value to minimize the differences.

BRIEF DESCRIPTION OF THE DRAWING

For a better understanding of the invention reference is made to the subsequent detailed description of the preferred embodiment thereof, taken in conjunction with the accompanying drawings, in which.

DESCRIPTION OF THE PREFERRED EMBODIMENTS

Figure 1:
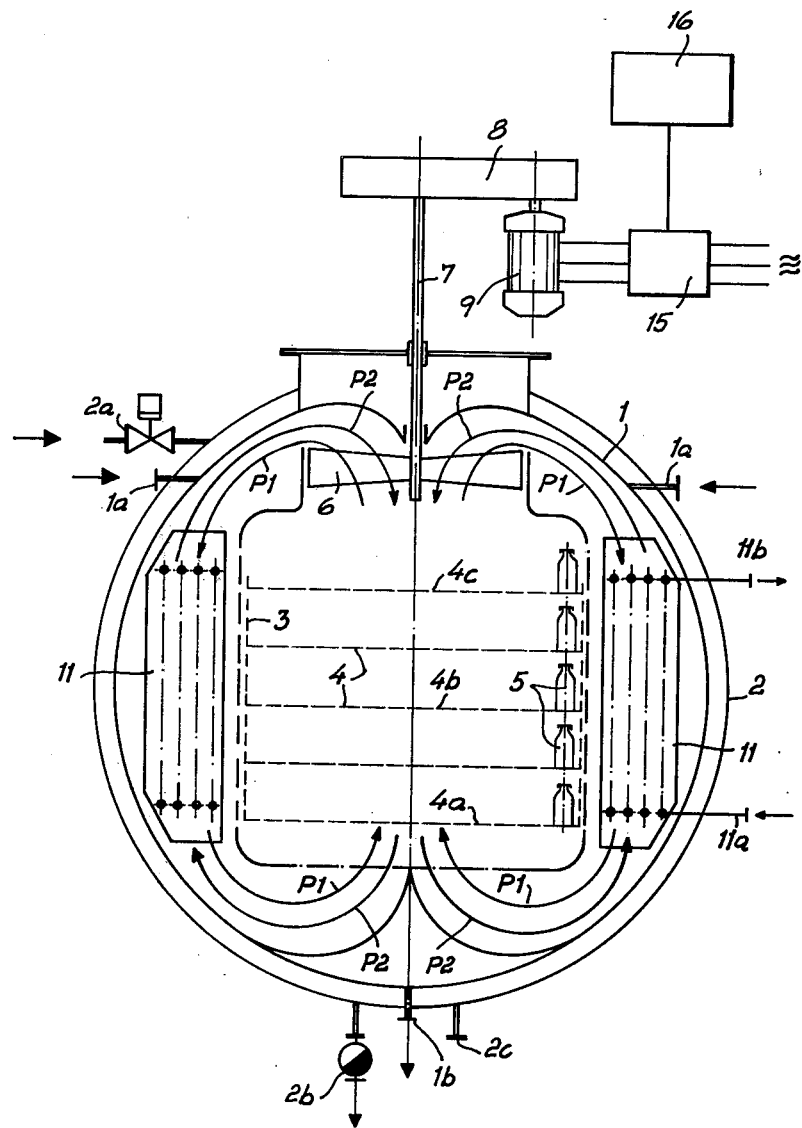
FIG. 1 is a schematic side section of a first embodiment of this invention, in which the direction of flow is periodically reversed.

Referring now to FIG. 1, the schematic representation of the sterilization apparatus includes a cylindrical housing 1, that is surrounded by a jacket 2 spaced therefrom, defining an interspace for a heating or cooling auxiliary fluid. Within the housing there is removably disposed a rack 3, having a plurality of open shelves 4 through which an operating fluid can flow, and which supports containers 5 filled with a substance to be sterilized.

At the top portion of the housing 1 is located a whirl fan 6 driven by an electromotor 9 via a shaft 7, and a belt drive 8. Cooling devices 11 are arranged between the housing 1 and the rack 3; the cooling device 11 is from time-to-time filled with a cooling medium, which medium is again discharged from time-to-time from the cooling device 11. Inlets 1a serve for introducing a hot steam-air mixture into the inner space of the apparatus housing 1, after the rack 3 with the containers 5 has been inserted, and the housing has been closed by a door or cover, for example. An outlet 1b is employed for discharging the condensates.

In known sterilization devices of the above-described type the operating medium is whirled around by means of a fan 6 in the sense of the arrows $P_1$ or $P_2$, in such a manner that the operating medium flows, for example, from below the rack 3 to there above substantially uniformly. Due to the fact that a hot operating medium transfers heat to the containers 5 during the heating-up period, and therefore is first cooled down, while streaming through the rack, and also due to the fact that the operating medium cooled down by the device removes heat from the containers during the cooling period, and consequently is warmed up by the flow of the medium through the rack, the containers arranged in the lowermost shelf 4a, in the middle shelf 4b, or in the uppermost shelf 4c are heated up, each at a different rate, and upon sterilization are again cooled at different speeds, as shown in the temperature vs. time diagrams $t_a$, $t_b$, and $t_c$ of FIG. 2a. The sterilization cycle lasts the entire charging time $T_C$ and includes the heating-up time $T_H$, the sterilization time $T_S$ and cooling-down time $T_K$. As the sterilization time $T_S$ can be counted only from the moment $T_H$, at which moment containers located at the uppermost shelf 4c have reached the sterilization temperature $t_s$, the individual containers during the entire charging time $t_c$ are subjected to the sterilization temperature for different time intervals, and consequently a non-uniform treatment will result, and in certain cases the containers may become damaged due to excessive exposure of the containers to the sterilization temperature.

This drawback is avoided in the embodiment of the present invention, according to FIG. 1, by connecting the electromotor 9 via a phase switch 15 to a three phase alternating current network, and by controlling the phase switch 15 by the timing-and controlling-device 16 in such a manner that the rotational direction of the electromotor is periodically reversed for time intervals that are short relative to the heating-up period $T_H$, or the cooling-down period $T_K$. As a consequence the whirling movement of the operating medium through the rack 4 alternates in the direction of arrows $P_1$ and $P_2$, as indicated in FIG. 1. In this way the characteristic curves of the temperature during the heating-up time and the cooling-down time follow a single average value $t'$ as indicated in FIG. 2b, so that the heating-up time and the cooling-down time, and therefore the whole charging time $T_C$ are substantially reduced, in spite of the fact that the sterilization time remains the same; the reduced time periods are indicated in FIG. 2b by $T'_H$, $T'_K$ or $T'_C$.

Instead of reversing the direction of the whirling stream of the operating medium by reversing the rotation of the driving motor for the fan, as explained above, with reference to FIG. 1, the timing and controlling device 16 may also control the angular adjustment of the blades of the fan 6 in a sense so as to cyclically reverse the effective operative direction of the fan. Another reduction of the heating-up and cooling-down times, and of the charging time to values $T''_H$, $T''_K$, or $T''_C$ in FIG. 2c is attained in the embodiment of FIG. 1 by introducing, through the inlet $2a$, saturated steam into the interspace between the jacket 2 and the housing 1, prior to the insertion into the housing 1 of the rack 3 containing articles to be sterilized. Upon placement of the rack 3 into the housing 1, it is nessary to heat up only the substance to be sterilized by the steam-air mixture introduced through the inlets $1a$. The precipitated condensate is discharged from the outlet $2b$.

In a similar manner the cooling of the substance to be sterilized can be achieved more quickly by introducing cooling water through the inlet $2c$ into the interspace between the jacket 2 and the housing 1, following the expiration of the sterilization time $T_S$, so that the outlet $2b$ is first closed, but upon expiration of the cooling time is again opened to discharge the cooling water.

Figure 2A:
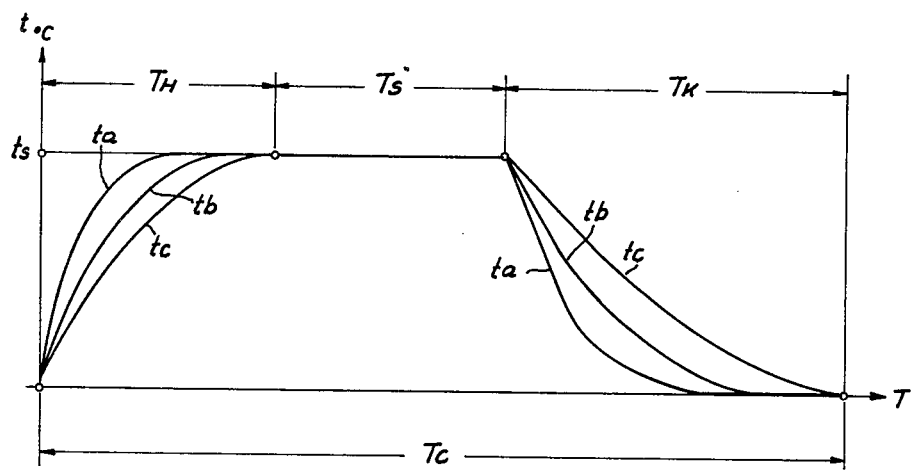
FIG. 2a is a temperature vs. time diagram explaining the operation of prior art sterilization devices.
Figure 2B:
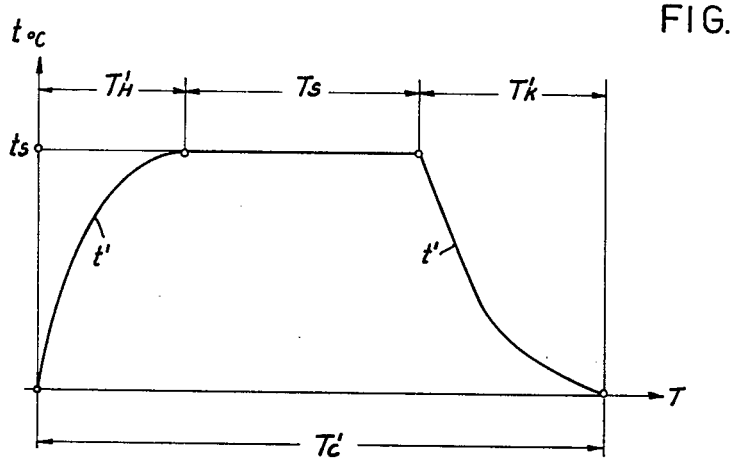
FIG. 2b shows a temperature vs. time diagram of the improved operation of the apparatus of this invention.
Figure 2C:
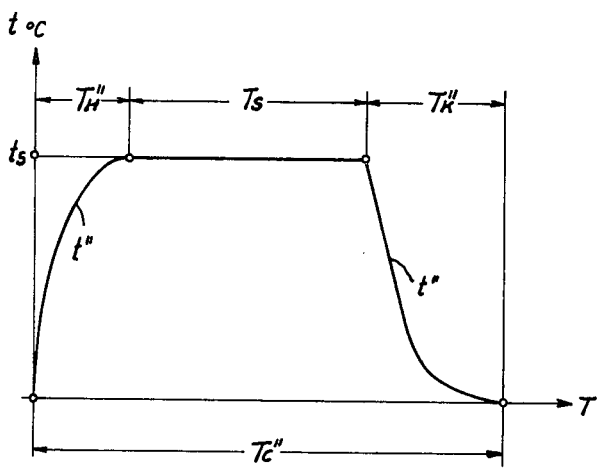
FIG. 2c is a temperature diagram of a preferred embodiment of the apparatus of this invention.

By this means, as seen in FIG. 2c on characteristic curves $t''$, a faster heating-up or cooling-down time will result, so that in comparison with the state of the art shown in the diapram of FIG. 2a, the total sterilization time and the charging time is reduced two-fold due to the reduction of both the heating-up, and the cooling-down intervals. In a sterilization process having a sterilization temperature of 120 degrees centigrade and a sterilization time $T_S$ of 30 minutes, the heating-up time, the cooling-down time, and the charging time can be reduced, in comparison with the process according to FIG. 2a, by applying the process of the present invention (FIG. 2b or FIG. 2c) as follows:

Heating-up time: $T_H=35$ min. $T_H'=25$ min. $T_H''=15$ min.

Cooling-down time: $T_K=45$ min. $T_K'=35$ min. $T_K''=30$ min.

Charging time: $T_C=110$ min. $T_C'=90$ min. $T_C''=75$ min.

Figure 3A:
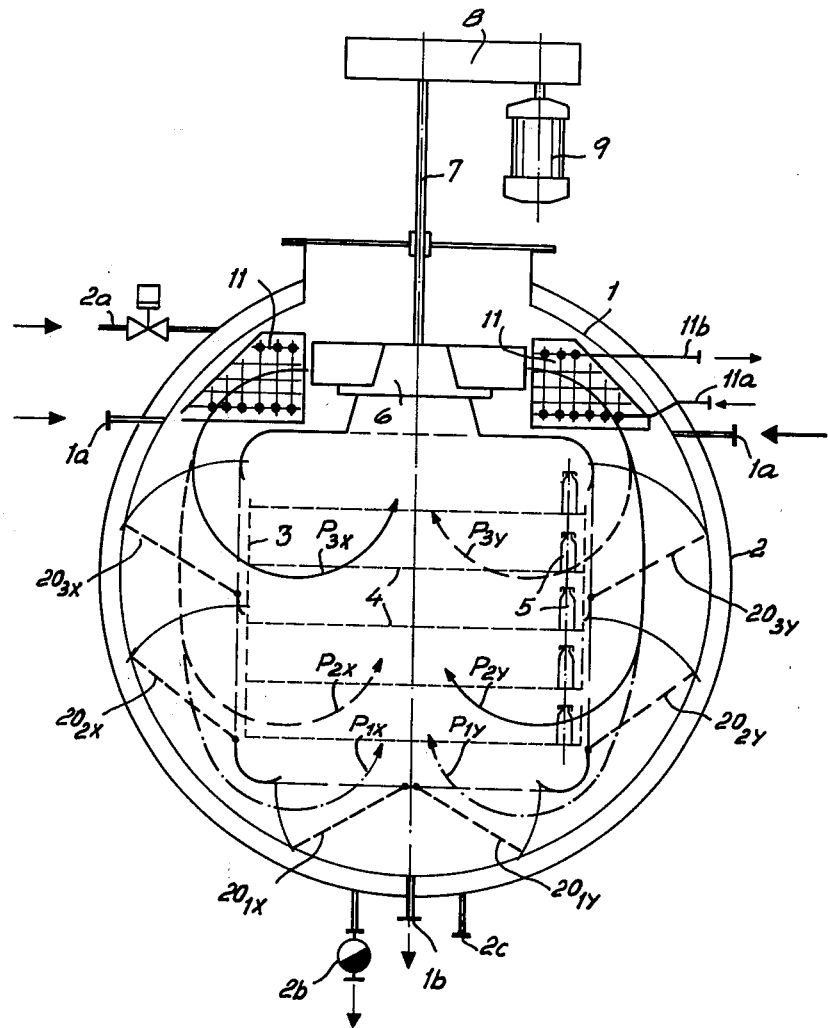
FIG. 3a is a schematic sectional side view of another embodiment of the present invention, where two partial streams of the operating medium are sequentially introduced into the support rack from two opposite sides thereof.
Figure 3B:
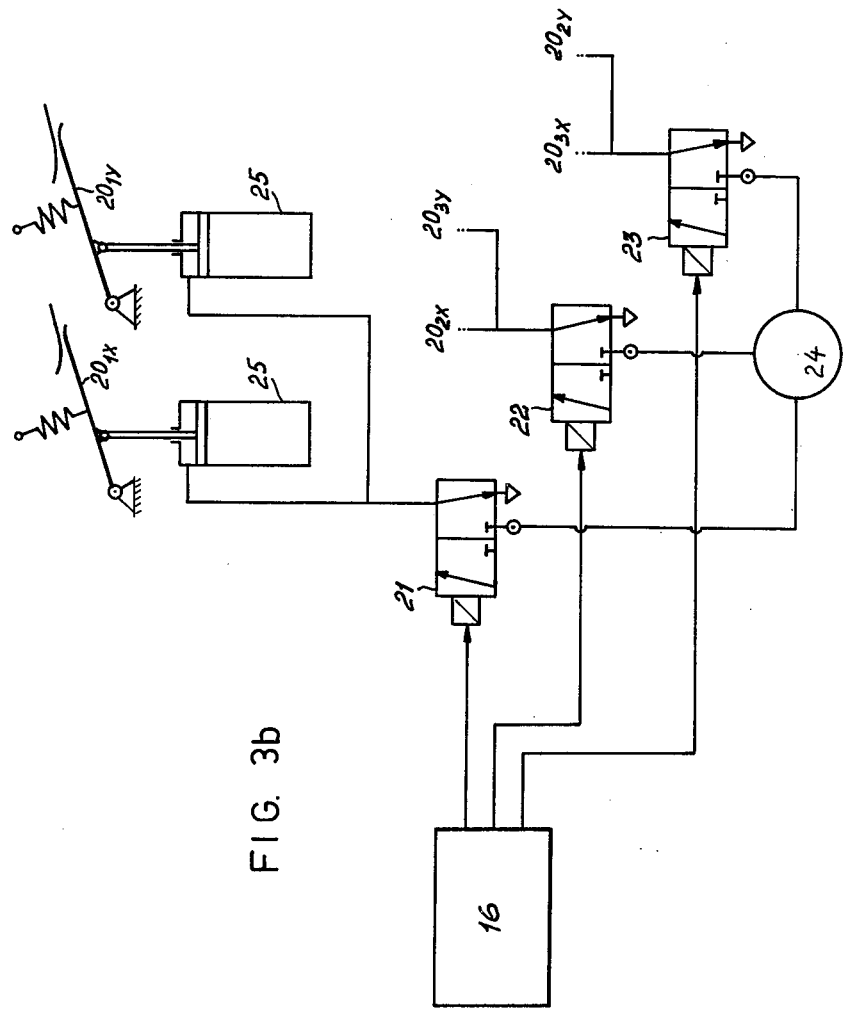
FIG. 3b is a schematic diagram of an example of the timing and controlling device of the present invention.

Another embodiment of this invention is illustrated in FIGS. 3a and 3b, where like components are denoted by the same reference numerals. In contrast to the embodiment of FIG. 1, the fan 6 in the apparatus of FIG. 3a always operates in the same effective direction, and the cooling device 11 is arranged in a radially extending stream path from the fan 6. Whereas in the example of FIG. 1 there is provided a stable path of the steam of the operating medium, in the example of FIG. 3a there are created three partial streams on each side of the sterilization chamber, namely partial streams indicated by arrows $P_{1x}$, $P_{2x}$, $P_{3x}$, and $P_{1y}$, $P_{2y}$, $P_{3y}$. The operating medium is divided into the partial streams by means of switching or shifting control members that in the given example are in the form of valves or lids $20_{1x}$, $20_{2x}$, $20_{3x}$, and $20_{1y}$, $20_{2y}$, $20_{3y}$. This arrangement makes it possible, for instance, by opening two selected valves, to produce substantially symmetrical, and axial partial streams of the operating medium. By opening another selected pair of the valves, the partial streams can be directed transversely and/or in opposite directions through the rack 3. An axial stream corresponding to arrows $P_{1x}$ and $P_{1y}$ occurs on opening the valves $20_{1x}$ and $20_{1y}$, a transverse or oblique stream, corresponding to arrows $P_{2x}$ and $P_{3y}$ takes place after opening valves $20_{2x}$ and $20_{3y}$, and another oblique stream corresponding to arrows $P_{3x}$ and $P_{2y}$ results by opening the valves $20_{3x}$ and $20_{2y}$. As disclosed in FIG. 3b, the alternate opening of valves can be controlled by the timing and controlling device 16, that transmits a succession of electrical pulses to pneumatic valves 21, 22 and 23, which allow a pressure air source 24 to alternately transmit compressed air to a pair of pneumatic cylinders 25; the pistons of the cylinders are linked to an assigned pair of valves as indicated only schematically in FIG. 3a. The valves in the housing 1, such as for example, valves $20_{1x}$ and $20_{1y}$, are spring-biased towards the closing position, and by the application of the controlling pulses the pistons act against the tension springs and open the valves 20 during operation of the controlling device 16.

Figure 4:
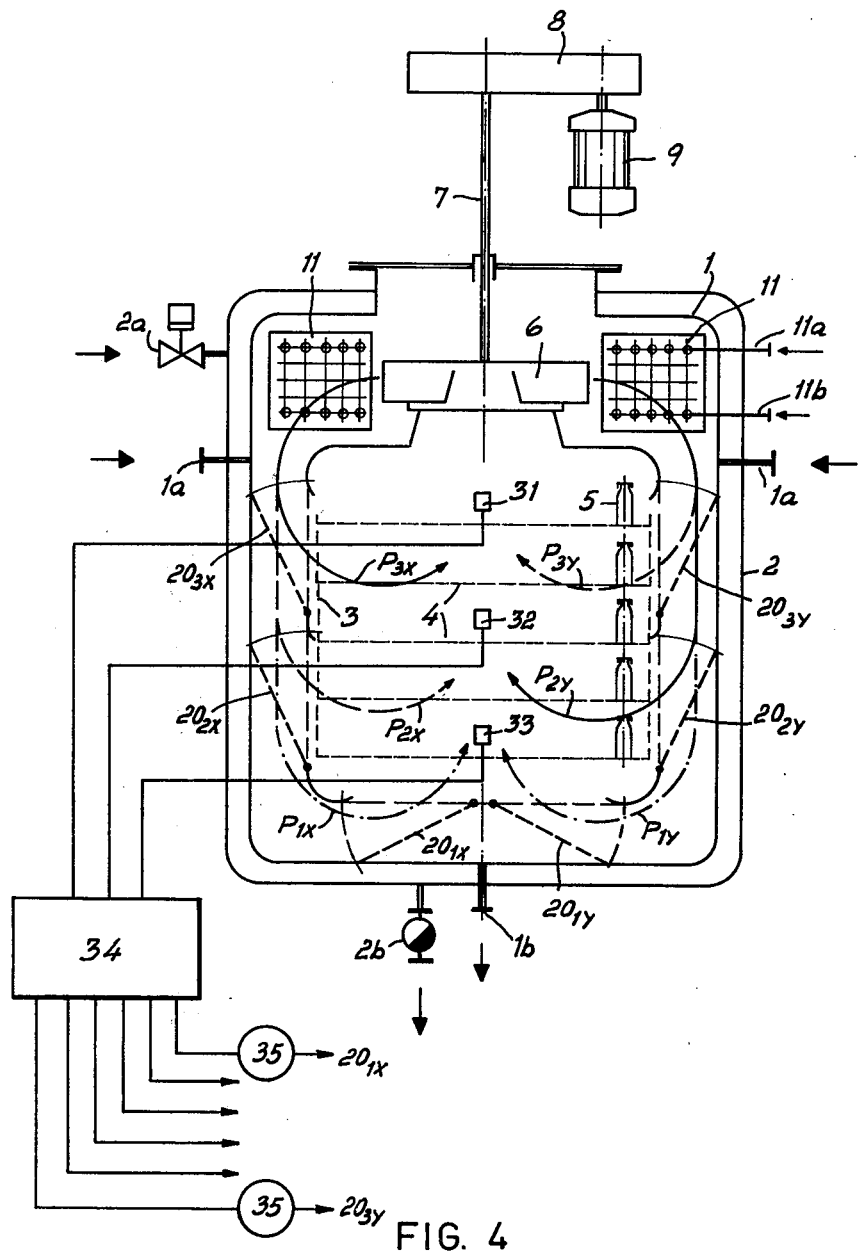
FIG. 4 is a schematic sectional side view of still another embodiment of the present invention, wherein a plurality of partial streams of the operating medium are simultaneously introduced from different directions into the container supporting rack.

In the embodiment according to FIG. 4, the apparatus housing 1 has a prismatic configuration, and is provided with a system of valves or lids 20 operating in a similar manner as those in FIG. 3a. The paths of partial streams are also indicated by arrows $P_{1x}$, $P_{2x}$, $P_{3x}$, $P_{1y}$, $P_{2y}$, and $P_{3y}$. Contrary to the embodiment of FIG. 3a, the valves 20 in FIG. 4 are not cyclically and alternately opened and closed, but are adjusted by means of valves and servomotors 35 in response to processed signals from temperature sensors 31, 32 and 33 arranged in different places in the rack 3. The signals from the sensors are first applied to a computer or a data processor 34, that processes the received signals, and in turn commands the valves and servomotors 35, so as to achieve a uniform average temperature of the operating medium in the whole region of the sterilization chamber. To this end the computer 34 compares the different temperature readings with one another, and delivers an output control signal to the servomotors 35, which motors are coupled to the valves $20_{1x}$, $20_{2x}$, $20_{3x}$, $20_{1y}$, $20_{2y}$ and $20_{3y}$ and adjust the same either individually or in groups, so that the region having the lowest temperature during the heating-up period is heated by a more powerful partial stream of the heating medium, or in cooling down the region having the highest temperature, is cooled by a more powerful stream of the cooling medium. The data processor for this purpose can be of any suitable well known conventional type in the art, and need not therefore be explained in detail.

While this invention has been explained and illustrated as embodied in a specific examples of a sterilization apparatus, it is not intended to be limited to the details shown, since various modifications and structural changes may be made without departing in any way from the spirit of the present invention. For example, the total charging time $T_C$ in the embodiment of FIGS. 3a and 4 can be further cut down by separate heating and cooling of the mass of the apparatus, and of the containers with the substance to be sterilized.

What is claimed as new and desired to be protected by Letters Patent is set forth in the appended claims:

1. In a process of sterilizing articles stacked on different levels in a closed chamber for a sterilization cycle, said sterilization cycle including heating-up and cooling-down periods, wherein the improvement comprises the steps of:
   introducing a stream of a heated sterilization fluid into said chamber;
   moving said fluid around said articles; and
   periodically changing the direction of said stream for time periods that are short relative to the heating-up and cooling-down periods of the sterilization cycle.

2. In a process as claimed in claim 1, wherein the improvement further comprises the steps of dividing the stream of said fluid into at least two partial streams, and periodically directing said partial streams to the different levels of the stacked articles.

3. In a process according to claim 2 wherein the improvement further comprises the steps of:
   sensing the temperature on said different levels,
   comparing the sensed values to a predetermined average temperature, and
   directing said partial streams to said levels in response to corresponding differences between said sensed values and said predetermined average value to minimize said differences.

4. A sterilization apparatus comprising in combination:
   an openable and closeable housing for articles to be sterilized therein;
   support means to support said articles in said housing;
   means operable for introducing a heated sterilization fluid into said housing to sterilize said articles during a predetermined sterilization period;
   propulsion means operable for moving said fluid in a continuous flow near said articles in said housing;
   a cooling device at least partially disposed in said housing for cooling the articles during a cooling period following said sterilization period; and
   timing and controlling means for changing the direction of continuous flow of said fluid at time intervals that are short relative to the sterilization and cooling periods.

5. An apparatus according to claim 4, wherein said propulsion means is a fan having angularly adjustable blades of predetermined positions, said positions being controllable by said timing and controlling means for alternately changing said direction of the fluid during said short time intervals.

6. An apparatus as defined in claim 5, wherein said timing and controlling means includes a reversible driving motor for said fan.

7. An apparatus as defined in claim 4, further including a jacket surrounding said housing and defining an interspace between said jacket and said housing.

8. An apparatus as defined in claim 7, wherein said jacket includes an inlet and an outlet for introducing into said interspace first a heating medium and subsequently a cooling medium, whereby said medium-filled interspace is heatable to a predetermined sterilization temperature prior to the insertion of the articles into said interspace, and is coolable following sterilization of the articles to a predetermined discharge temperature of the articles.

9. A sterilization apparatus comprising in combination:
   an openable and closeable housing for articles to be sterilized therein;
   support means to support said articles in said housing at various regions;
   means operable for introducing a heated sterilization fluid into said housing to sterilize said articles during a predetermined sterilization period;
   propulsion means operable for moving said fluid in a continuous flow near said articles in said housing;
   a cooling device at least partially disposed in said housing for cooling the articles during a cooling period following said sterilization period; and
   timing and controlling means for changing the direction of continuous flow of said fluid, for dividing the flow of said fluid in said housing into at least two partial streams, and for periodically directing said partial stream to different, regions in said housing, whereby a relative high uniformity of heat transfer for sterilization between said fluid and the articles at said regions in said housing is attained.

10. An apparatus as defined in claim 9, wherein the timing and controlling means includes a plurality of valves successively arranged within the path of said partial streams, and wherein said timing and controlling means alternately opens and closes said valves to direct said partial streams towards said support means.

11. An apparatus as defined in claim 10, further including a plurality of temperature sensors respectively located at different regions in said housing for measuring temperature values, and a data processor coupled to said sensors and to said timing and controlling means for controlling said valves in response to the values measured by said temperature sensors.

* * * * *